US012564508B2

(12) United States Patent
Bauerfeind et al.

(10) Patent No.: US 12,564,508 B2
(45) Date of Patent: Mar. 3, 2026

(54) BANDAGE FOR THE WRIST JOINT OR THE ANKLE JOINT

(71) Applicant: BAUERFEIND AG, Zeulenroda-Triebes (DE)

(72) Inventors: Hans B. Bauerfeind, Zeulenroda-Triebes (DE); Toni Bogusch, Zeulenroda-Triebes (DE)

(73) Assignee: BAUERFEIND AG, Zeulenroda-Triebes (DE)

( * ) Notice: Subject to any disclaimer, the term of this patent is extended or adjusted under 35 U.S.C. 154(b) by 23 days.

(21) Appl. No.: 18/576,735

(22) PCT Filed: Jul. 1, 2022

(86) PCT No.: PCT/EP2022/068301
§ 371 (c)(1),
(2) Date: Jan. 4, 2024

(87) PCT Pub. No.: WO2023/280718
PCT Pub. Date: Jan. 12, 2023

(65) Prior Publication Data
US 2024/0285423 A1 Aug. 29, 2024

(30) Foreign Application Priority Data
Jul. 6, 2021 (DE) .......................... 102021207095.7

(51) Int. Cl.
A61F 5/01 (2006.01)

(52) U.S. Cl.
CPC ........... A61F 5/0118 (2013.01); A61F 5/0111 (2013.01)

(58) Field of Classification Search
CPC ........ A61F 5/0118; A61F 5/0111; A61F 5/01; A61F 5/0127; A61F 13/066;
(Continued)

(56) References Cited

U.S. PATENT DOCUMENTS 4,495,942 A 1/1985 Palumbo
4,702,234 A 10/1987 Huntjens
(Continued)

FOREIGN PATENT DOCUMENTS

DE 2712509 A1 3/1978
DE 20005742 U1 8/2001
(Continued)

OTHER PUBLICATIONS

Federal Service for Intellectual Property (Rospatent), "Office Action," and Search Report for Russian Patent Application No. 2024102728/14, May 7, 2025.
(Continued)

*Primary Examiner* — Daniel A Miller
(74) *Attorney, Agent, or Firm* — Dentons Durham Jones Pinegar; Sarah W. Matthews

(57) ABSTRACT

The present invention relates to a joint bandage for a wrist or an ankle with a strap element, wherein the strap element has at least two elastic sections and at least one non-elastic section between the two elastic sections, wherein the second end of the strap element is reversibly fastenable to the strap element or to a tube element and/or wherein the strap element is at least 40 cm long.

14 Claims, 15 Drawing Sheets

(58) Field of Classification Search
CPC ..... A61F 2005/0167; A61F 2005/0169; A43B 7/14; A43B 7/20; A43B 7/144; A47B 21/0371; A63B 71/14; A41D 13/088
USPC .......................................................... 602/21
See application file for complete search history.

(56) References Cited

U.S. PATENT DOCUMENTS

| | | | |
|---|---|---|---|
| 2010/0069802 A1 | 3/2010 | Motyer | |
| 2020/0093628 A1* | 3/2020 | Sigurdsson | .............. A43B 7/20 |
| 2021/0022900 A1 | 1/2021 | Hebenstreit et al. | |

FOREIGN PATENT DOCUMENTS

| | | |
|---|---|---|
| DE | 202014005449 U1 | 7/2014 |
| EP | 2491895 A1 | 8/2012 |
| EP | 2612631 B1 | 9/2014 |
| JP | 6268457 A | 3/1987 |
| JP | 2019033998 A | 3/2019 |
| RU | 2752599 C1 | 7/2021 |

OTHER PUBLICATIONS

Federal Service for Intellectual Property (Rospatent), Search Report for Russian Patent Application No. 2024102728/14, May 7, 2025.

European Patent Office acting as International Searching Authority, "International Preliminary Report on Patentability," for International Application No. PCT/EP2022/068301, Jan. 11, 2024 (English translation only).

Germany Patent Office, "Search Report," for German Application No. 10 2021 207 095.7.

European Patent Office acting as International Searching Authority, "International Search Report and Written Opinion," for International Application No. PCT/EP2022/068301, Oct. 26, 20222.

European Patent Office acting as International Searching Authority, "International Preliminary Report on Patentability," for International Application No. PCT/EP2022/068301, May 22, 2023.

Japan Patent Office, "Notice of Reasons for Rejection," Japanese Patent Application No. 2024-500172, Aug. 20, 2025.

* cited by examiner

200 ⟶

210

250

BANDAGE FOR THE WRIST JOINT OR THE ANKLE JOINT

CROSS REFERENCE TO RELATED APPLICATIONS

This application is a U.S. a national stage application under 35 U.S.C. 371 of PCT/EP2022/068301 ("the '301 PCT application"), filed Jul. 1, 2022, which claims priority to German patent application DE 10 2021 207 095.7 filed Jul. 6, 2021 ("the '095.7 Priority Application"). The contents of the '301 PCT Application and '095.7 Priority Application are incorporated herein in their entireties.

SUMMARY

The present invention relates to a joint bandage for a wrist or an ankle with a strap element.

Extremity end joints, i.e. the wrist and ankle, which movably connect the zygopodium, i.e. the forearm or lower leg, to the basipodium and metapodium, i.e. the hand or foot, are susceptible to overloading and degenerative diseases, for example during sport or due to ageing, which can lead to pain. Therefore, these joints are often bandaged as a prophylactic or therapeutic measure.

A wide variety of wrist and ankle bandages are known in the state of the art. These are often based on a tubular knitted fabric, wherein a short compression strap running around the wrist can be associated to the knitted fabric, as shown in DE 20 2012 004 652 U1 or EP 2090 273 A2. These bandages often also have an associated stabilising bar to fix the flexion movement. With such bandages, there is always a discrepancy between a high degree of stabilisation and a high degree of freedom of movement at the same time. The stabilisation bars are also often perceived as a nuisance. In particular during temporary sporting activities such as volleyball or handball, but also during daily activities such as cycling or driving, such bars are a hindrance.

The present invention underlies the technical problem of providing joint bandages, in particular wrist bandages and ankle bandages, which have improved functionality and which, in particular, allow a high degree of stabilisation of the joint while at the same time ensuring a high degree of freedom of movement. The bandage should nevertheless be as simple as possible and thus also ensure good manageability, in particular when applying the bandage.

The present invention solves the underlying technical problem by the subject matter of the independent claims.

The present invention relates to a joint bandage for a wrist or an ankle, comprising a strap element with a first end and a second end, wherein the strap element has at least two elastic sections and at least one non-elastic section between the two elastic sections, wherein the second end of the strap element is fastened or reversibly fastenable to the strap element or to a tube element.

The present invention also relates to a joint bandage for a wrist or an ankle, comprising an elastic tube element and a strap element, wherein the tube element has a first tube half with a first end and a second tube half with a second end, wherein the strap element has a first end and a second end, wherein the first end of the strap element is fastened or fastenable to the first tube half, wherein the second end of the strap element is reversibly fastenable to the strap element or to the first tube half, characterised in that, in the applied state, the first end of the strap element is fastened to the first tube half and is positioned on the zygopodium and the strap element runs from the first end distally over the extremity end joint to the basipodium, runs around the basipodium or metapodium on the inside, runs dorsally over the extremity end joint to the zygopodium and thereby crosses itself, runs around the zygopodium and is reversibly fastened to the strap element or to the first tube half with the second end in the area of the zygopodium.

The present invention also relates to a joint bandage for extremity end joints, i.e. for wrists or ankles, comprising an elastic tube element and a strap element, wherein the tube element has a first tube half with a first end and a second tube half with a second end, wherein the strap element has a first end and a second end, wherein the first end of the strap element is fastened or fastenable to the first tube half, wherein the second end of the strap element is fastened or reversibly fastenable to the strap element or to the first tube half, characterised in that the strap element is at least 40 cm long.

It has been shown that the strap elements of the bandage according to the invention can be applied to the wrist or ankle in such a way that an advantageous stabilisation of the joint is achieved by the strap element itself, so that a stabilising bar can be dispensed with if necessary and the strap elements allow good freedom of movement despite the stabilisation. The movement of the hand or foot into the restricted/supported areas permitted by the strap element is connected with an increasing amount of work to overcome the counterforce generated by the bandage. The strap elements of the bandage according to the invention allow applying to the forearm/hand or to the lower leg/foot in an advantageous course, which lead to a significantly increased stabilisation compared to a strap simply running around the joint, even without a stabilising bar.

In the context of the present invention, an extremity end joint summarises the wrist and the ankle, also known as the foot joint. The zygopodium summarises the forearm and lower leg, the basipodium summarises carpus and tarsus and the metapodium summarises metacarpus and metatarsus. The present invention relates to bandages for humans but also for other mammals.

The present invention relates to both medical joint bandages and sports bandages. The present invention relates to wrist bandages and/or ankle bandages.

The joint bandage according to the invention may be provided with a tube element or without a tube element.

In a first embodiment, the joint bandage according to the invention is provided without a tube element and preferably comprises only the strap element.

In this first embodiment, the invention relates in particular to a joint bandage for a wrist or an ankle, comprising a strap element with a first end and a second end, wherein the strap element has at least two elastic sections and at least one non-elastic section between the two elastic sections, wherein the second end of the strap element is fastened or preferably reversibly fastenable to the strap element.

Preferably, the strap element has a fixation section which can run around the zygopodium, in particular the forearm or the lower leg, and the fixation section has two interconnectable areas, so that the fixation section is fixable to the zygopodium, in particular the forearm or the lower leg, by connecting the two areas. The strap element can thus be centered on itself by means of ring formation/ring bandage on the wrist and thus forms its own "anchor" for fixing the strap element to itself.

Preferably, the strap element has a first end and a second end, wherein the first end of the strap element is formed by the fixation section and is fastenable to the zygopodium, wherein the second end of the strap element is reversibly fastenable to the strap element, wherein, in the applied state, the first end of the strap element is positioned on the zygopodium by the fixation section and the strap element runs from the first end distally over the extremity end joint to the basipodium, runs around the basipodium or metapodium on the inside, runs dorsally over the wrist or ankle to the zygopodium and thereby crosses itself, runs around the zygopodium and is reversibly fastened to the strap element with the second end in the area of the zygopodium.

In an alternative embodiment, a tube element is associated to the strap element. Such tube elements are known to those skilled in the art. Preferably, the tube element bridges the wrist or the ankle.

The invention thus also relates to a joint bandage for a wrist or ankle, comprising a tube element and a strap element with a first end and a second end, wherein the strap element has at least two elastic sections and at least one non-elastic section between the two elastic sections, wherein the second end of the strap element is reversibly fastenable to the strap element or to a tube element.

The invention thus also relates to a joint bandage comprising an elastic tube element and a strap element, wherein the tube element has a first tube half with a first end and a second tube half with a second end, wherein the strap element has a first end and a second end, wherein the first end of the strap element is fastened or fastenable to the first tube half, wherein the second end of the strap element is reversibly fastenable to the strap element or to the first tube half, and wherein the strap element is at least 40 cm long.

The invention also relates to a joint bandage for a wrist or an ankle, comprising an elastic tube element and a strap element, wherein the tube element has a first tube half with a first end and a second tube half with a second end, wherein the strap element has a first end and a second end, wherein the first end of the strap element is fastened or fastenable to the first tube half, wherein the second end of the strap element is reversibly fastenable to the strap element or to the first tube half, characterised in that, in the applied state, the first end of the strap element is fastened to the first tube half and is positioned on the zygopodium and the strap element runs from the first end distally over the extremity end joint to the basipodium, runs around the basipodium or metapodium on the inside, runs dorsally over the extremity end joint to the zygopodium and thereby crosses itself, runs around the zygopodium and is reversibly fastened to the strap element or to the first tube half with the second end in the area of the zygopodium.

The tube element is preferably made of neoprene, a woven fabric or knitwear, for example a knitted fabric or a knitting. Preferably, the tube element has a proximal opening. Distally, the tube element can either have a distal opening or be designed as a glove or stocking. Preferably, the tube element also has a separate opening for the thumb or the big toe.

Preferably, the joint bandage has no stabilising bar. Surprisingly, it has been shown that the joint bandage according to the invention, in particular with a tube element, can dispense with a stabilising bar and still achieve sufficient stability thanks to the strap guiding made possible by the strap element according to the invention. However, it may be possible to additionally provide for the possibility of inserting a stabilising bar into the joint bandage, in particular the tube element, at least temporarily, if required.

The joint bandage can have a tensioning element on the tube element. This tensioning element can be used to pre-form and/or tension the body of the tube element so that the tube element can be put on more easily. Even if the tensioning element can be designed as a bar, it is not a stabilising bar, as the tensioning element does not, should not and cannot assume a stabilising function of the joint due to its form and positioning on the joint bandage, but only prevents the tube element from deforming in an undesirable way, in particular from being compressed.

The tube element can be equipped with pads if required.

Preferably, the strap element is at least 40 cm long. When the joint bandage is in the put-on state, a strap element that is at least 40 cm long allows a strap course around the forearm/lower leg, hand/foot and joint located therebetween in accordance with the present invention.

The first end of the strap element is fastened either to the tube element or to itself in the area of the zygopodium. The fastening of the first strap element can be reversible, for example via a Velcro® (i.e., hook-and-loop fastener) fastener or via press studs, or the strap element can be permanently fastened with its first end to the tube element or permanently fastened to itself so that it forms a loop. The strap element then runs around the extremity end joint as described at present.

Preferably, the second end of the strap element is reversibly fastenable to the strap element or to a tube element. The reversible fastening makes it possible to loosen the fastening and, in an advantageous manner, to tighten the strap element, for example if areas are provided on the strap element and/or on the tube element which allow the second end of the strap element to be positioned differently, for example Velcro® (i.e., hook-and-loop fastener) fastening areas.

Preferably, the strap element has at least two elastic sections and at least one non-elastic section between the two elastic sections. Preferably, the strap element has alternating elastic and non-elastic sections. In the case of a completely elastic stretchable strap element, unpleasant constrictions can occur, especially in the area of the thumb or big toe. With a completely inelastic strap element, the hand or foot is fixed too tightly and an adjustability of the stabilisation cannot be ensured. A combination of elastic and non-elastic sections in the strap element makes it possible to overcome these problems in an advantageous manner.

Preferably, the elastic sections of the strap element are elastically stretchable. The elastically stretchable sections enable the strap element to expand at certain sections when it is tensioned by pulling the strap element when the bandage is applied, and the strap element returns to a relaxed basic state when the bandage is taken off.

Preferably, at least one elastic section of the strap element runs non-orthogonally to the pivot axis of the wrist or ankle that is to be influenced. Preferably, at least one elastic section of the strap element runs at an angle of 30 to 180 degrees, more preferably of 35 to 170 degrees, particularly preferably of 40 degrees to 50 degrees, in particular of about 45 degrees to the pivot axis.

Preferably, an elastic section of the strap element runs to the second end of the strap element or to an attachment area at the second end of the strap element.

Preferably, at least one elastic section of the strap element runs over the back of the hand or over the palm of the hand or over the back of the foot or the sole of the foot.

Preferably, at least one elastic section of the strap element runs over the back of the hand or the palm of the hand or over the back of the foot or the sole of the foot and/or at least one non-elastic section runs along the edges of the hand or the edge of the foot. Preferably, at least one non-elastic section runs along the edges of the hand or the edge of the foot.

Suitable materials for the strap element and for the elastic and inelastic sections of the strap element are known to the person skilled in the art.

Preferably, the strap element has at least one tapered section. The tapered section is positioned on the strap element so that it lies in the area of the thumb or big toe in the put-on state. The tapered section is therefore positioned in the area between the thumb and index finger or between the big toe and the adjacent toe and adapts to the narrow space between the fingers or toes in an advantageous manner due to the taper. The taper can take the form of an incised arch or be formed by a narrow section of the strap. Alternatively, the strap element can also have a hole at this position through which the thumb or big toe can be inserted.

The tapered section is preferably inelastic.

Preferably, the strap element has at least one section in the form of a parallelogram or a curvature or a kink. Preferably, the strap element has at least one section in the form of a parallelogram. The section in the form of a parallelogram or a curvature or kink forms a bevelled section in the course of the strap element, which leads to a particularly adapted course of the strap element in the joint area.

Preferably, the section in the form of a parallelogram or a curvature or kink is inelastic.

Preferably, there is an elastic section between the inelastic tapered section and the inelastic section in the form of a parallelogram or a curvature or a kink.

Preferably, the strap element has at least one tapered section and at least one section in the form of a parallelogram or a curvature or a kink.

Preferably, the strap element successively has a first elastic section, a first non-elastic section, a second elastic section, a second non-elastic section and a third elastic section, wherein the first non-elastic section has a section in the form of a parallelogram or a curvature or a kink and wherein the second non-elastic section has a taper.

Preferably, a non-elastic pre-section is further associated to the first elastic section.

Preferably, the strap element comprises at least two reversibly interconnectable strap part elements.

Preferably, the strap element comprises a first strap part element with the first end and a second strap part element with the second end, wherein the second strap part element is elastic.

Preferably, the first strap part element and the second strap part element are reversibly interconnectable via a third end on the first strap part element and a fourth end on the second strap part element, wherein preferably the fourth end on the second strap part element comprises a connecting element with which the second strap part element is reversibly fastenable to the tube element without the first strap part element. In this preferred embodiment, the second strap part element can be used without the first strap part element, for example as a cuff placed around the wrist or ankle. This allows the bandage to be advantageously adapted to the patient's rehabilitation process or the wearer's intensity of movement independently of rehabilitation, for example, by using both strap part elements as presently described in a first therapy step, then using only the second strap part element as a cuff around the wrist or ankle in a second optional therapy step and using the tube element as a compression cuff in a third optional therapy step. However, such an application and removal of the bandage with the first strap element is also advantageous in other ways, for example during sports or driving.

Of course, the strap element can also be designed as a single piece, for example if only prophylaxis or therapy with the strap course described here is desired.

A further embodiment of the joint bandage for a wrist or an ankle according to the invention comprises a strap element with a first end and a second end, wherein the strap element has at least two elastic sections and at least one non-elastic section between the two elastic sections, wherein the second end of the strap element is fastened or reversibly fastenable to the strap element. In this embodiment, a tube element may or may not be provided. In this embodiment, the strap element forms a loop which can run around the hand or foot, running between the thumb/big toe and the index finger/second toe. The elastic section of the strap is positioned on the palm of the hand or the outer surface of the hand or the inner surface of the foot or the outer surface of the foot, while the two inelastic sections are positioned on the edges of the hand or the edges of the foot, so that the position is secured and cutting is prevented. The loop is formed by connecting the second end of the strap element to a middle section of the strap element. From this connection area to the first end of the strap element, the strap element runs over the joint to the forearm or lower leg. At the forearm or lower leg, the first end of the strap element is either connected to a tube element, which can also be relatively short, or the first end of the strap element forms a fixation section as described above, with which the strap element is fastenable directly to the forearm or lower leg. The connection area of the strap can be positioned either on the upper side or the lower side of the hand or foot, depending on which direction of movement is to be limited.

The person skilled in the art can easily combine the elements described in the various embodiments of the joint bandage according to the invention.

Further preferred embodiments are shown in the examples, the figures and the sub-claims, without these being to be understood as limiting.

The movement of the hand or foot into the restricted/supported areas permitted by the strap element is connected with an increasing amount of work to overcome the counterforce generated by the bandage. The necessary force increases until the point at which no further movement in the restricted/supported direction is possible. From a certain joint position, a counterforce is generated by the strap guide, similar to a lasso, which tightens further under stress and thus fixes an object more firmly. Thus, in the embodiment shown, a stabilising bar can be dispensed with in an advantageous manner.

BRIEF DESCRIPTION OF THE DRAWINGS

It shows

DETAILED DESCRIPTION

Figure 1A:
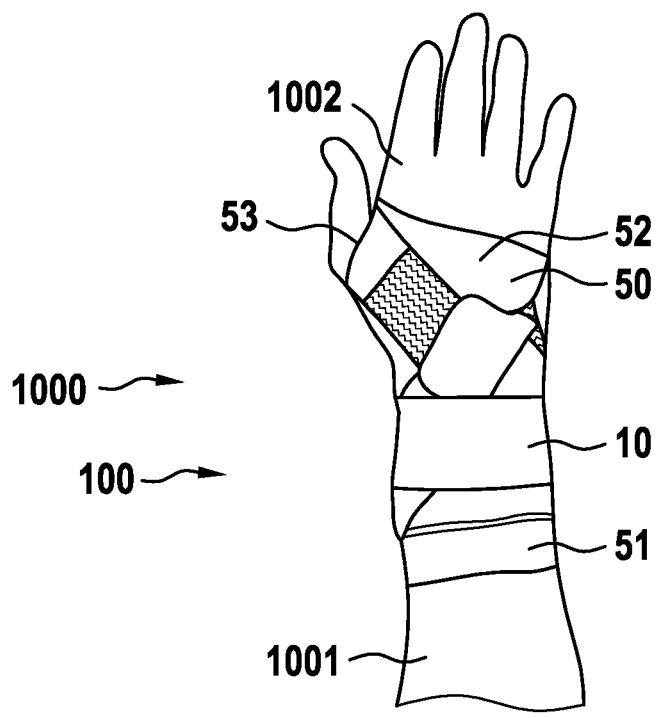
FIGS. 1a-1b an embodiment of a wrist bandage with tube element according to the invention FIGS. 2a-2b the first section of a strap element according to the invention FIGS. 3a-3b the second section of the strap element of FIG. 2
Figure 1B:
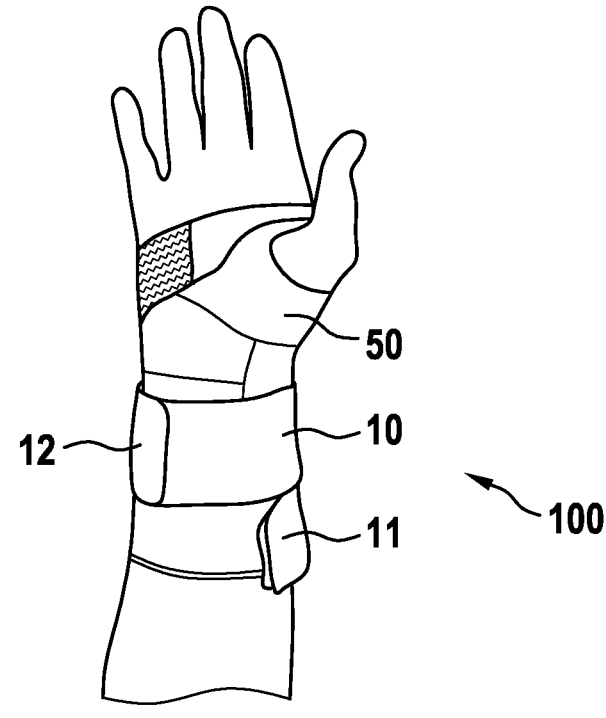

FIG. 1 shows a wrist bandage (100) according to the invention in the embodiment with tube element (50) on a right wrist (1000). A strap element (10) according to the invention is fastened to the tube element (50), which is placed around the area of the forearm (1001) adjacent to the wrist (1000), the wrist (1000) and the hand (1002) to stabilise the wrist (1000). FIG. 1a shows the wrist bandage (100) on the back of the hand and FIG. 1b shows the wrist bandage (100) on the palm of the hand. The tube element (50) has a first tube half with a first end (51) and a second tube half with a second end (52) with an additional opening (53) for the thumb, wherein the strap element (10) has a first end (11) and a second end (12), wherein the first end (11) of the strap element (10) is fastened to the first tube half (51) via a Velcro® (i.e., hook-and-loop fastener) connection, wherein the second end (12) of the strap element (10) is reversibly fastenable to the strap element (10) or to the first tube half (51) via a Velcro® (i.e., hook-and-loop fastener) connection and is presently fastened to the strap element (10). The first end of the strap element (10) is fastened to the first tube half (51) and positioned on the forearm (1001). The strap element (10) runs from the first end distally across the wrist (1000) to the back of the hand (1002), runs around the hand (1002) on the inside of the hand, then runs in the space between the thumb and index finger. From there, the strap element (10) runs dorsally back over the wrist (1000) to the forearm (1001), thereby crossing itself. The strap element (10) then wraps around the forearm (1001) and is Velcro® (i.e., hook-and-loop fastener) ed to itself with the second end (12) in the area of the forearm near the wrist. The force exerted by the strap element (10) can be adjusted by tensioning the strap element (10) and positioning the second end (12) accordingly. No stabilising bar is required for this bandage.

Figure 2A:
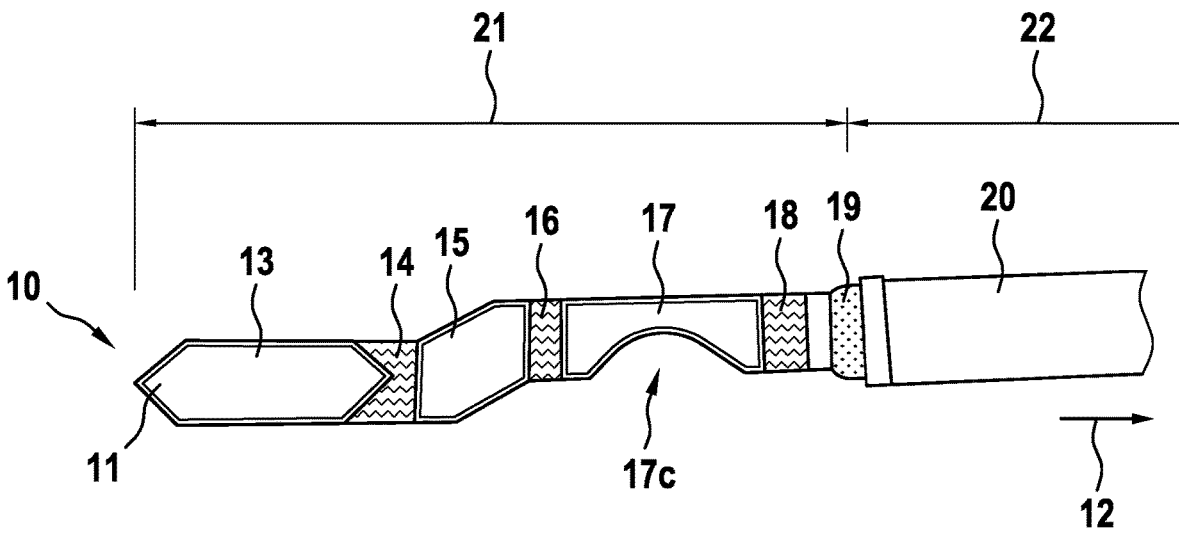
Figure 2B:
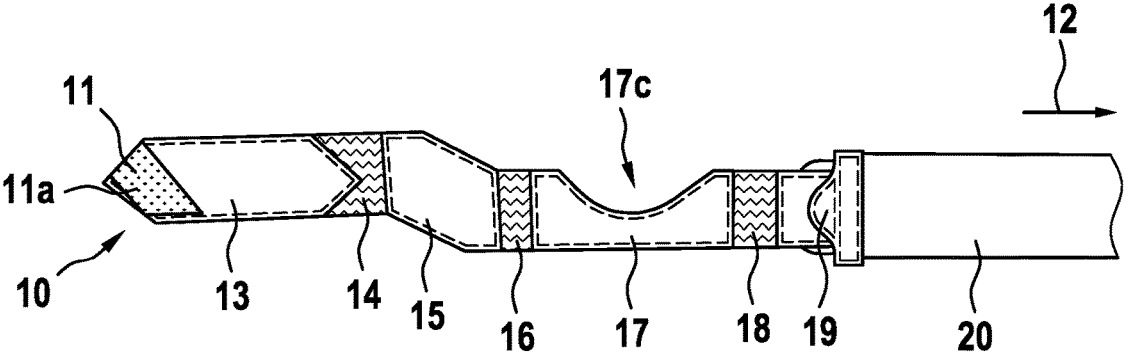

FIG. 2 shows the strap element (10) of the joint bandage according to the invention from FIG. 1. FIG. 2A shows the outside of the strap element (10) and FIG. 2B the inside of the strap element (10). The strap element (10) is approximately 64 cm long in the unstretched state and has several alternating elastic and inelastic sections. At the first end (11) there is a first inelastic section (13), with which the strap element is fastenable to the tube element via a Velcro® (i.e., hook-and-loop fastener) element (11a). This is followed by a first elastic section (14). This is followed by a second inelastic section (15), which is designed in the form of a parallelogram and thus leads to a shift of the course of the strap. This is followed by a short second elastic section (16), followed by a third inelastic section (17), which has a taper in the form of a cut-out arch (17c). In the applied state, this taper lies between the thumb and index finger so that the strap element (10) rests comfortably in this area. This is followed again by a short third elastic section (18), which is connected to a long fourth elastic section (20) via a Velcro® (i.e., hook-and-loop fastener) connection (19). The fourth elastic section (20) ends at the second end (12) of the strap element (10), which is no longer visible, with a Velcro® (i.e., hook-and-loop fastener) element.

The strap element (10) can be divided into a first part element (21) and a second part element (22) by the Velcro® (i.e., hook-and-loop fastener) connection (19).

The elastic sections (14, 16, 18, 20) of the strap element (10) allow the necessary stretching of the strap element (10) in the applied state, while the inelastic strap sections (13, 15, 17, 19) provide the necessary force transmission of the bandage and thus contribute to the stabilisation of the wrist. The inelastic sections serve in particular to impede or prevent the hand from moving into undesirable, in particular unhealthy, positions.

Figure 3A:
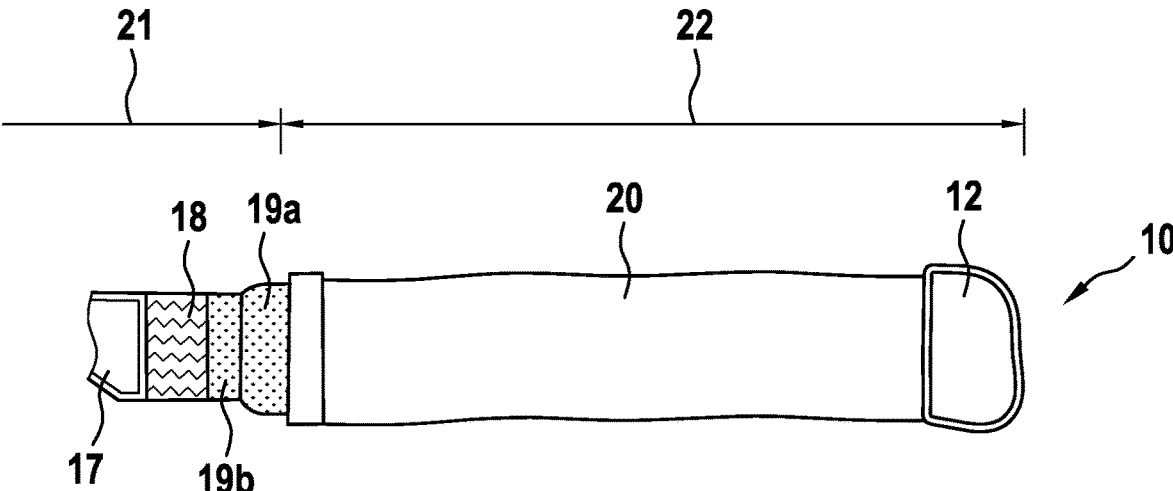
Figure 3B:
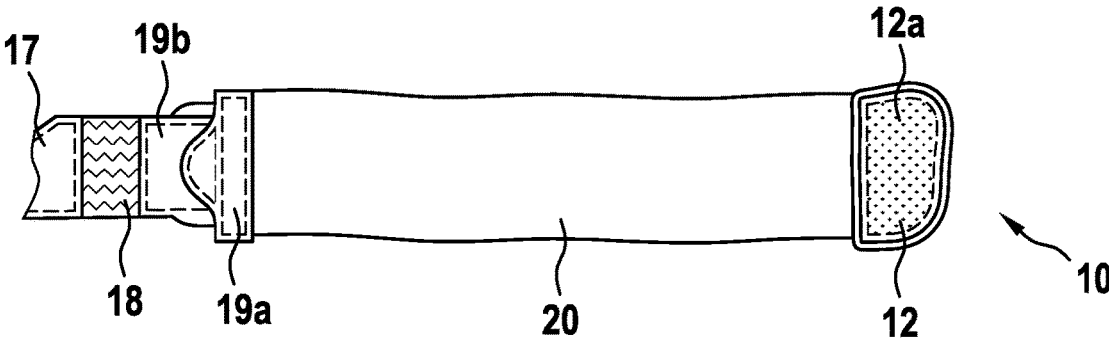

FIG. 3 shows the strap element (10) of the joint bandage according to the invention from FIG. 1. FIG. 3A shows the outside of the strap element (10) and FIG. 3B the inside of the strap element (10). The entire second part section (22) with the fourth elastic section (20), which ends at the second end (12) of the strap element (10) and the Velcro® (i.e., hook-and-loop fastener) element (12a) there, can be seen. The fourth elastic section (20) is reversibly connected by a Velcro® (i.e., hook-and-loop fastener) element (19a) to the Velcro® (i.e., hook-and-loop fastener) element (19b) of the first part section (21), which is not shown in its entirety, but in which only the third elastic section (18) and the end of the third inelastic section (17) can be seen.

Figure 4A:
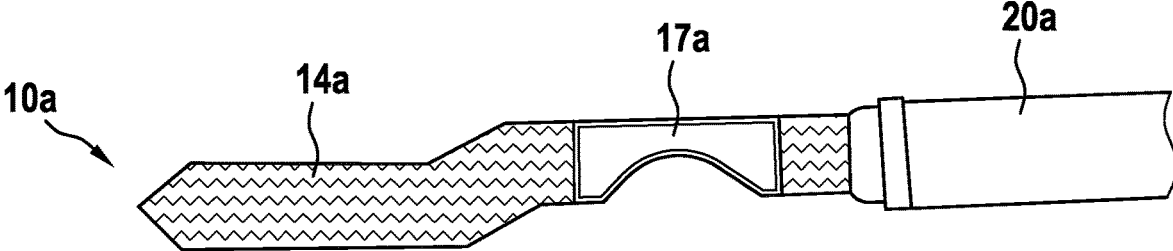
FIGS. 4a-4b two alternative embodiments of the strap element
Figure 4B:
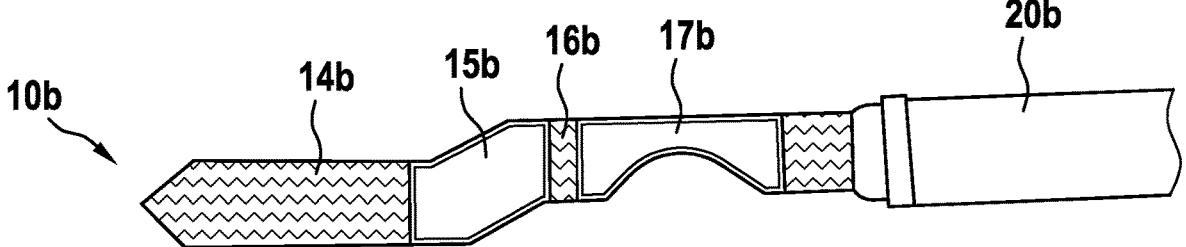

FIG. 4 schematically shows a first (10a) and a second (10b) alternative and simplified embodiment of the strap element of FIGS. 2 and 3. In FIG. 4a, the strap element (10a) comprises only a first elastic section (14a), a second elastic section (20a) and an intermediate inelastic section (17a) with the taper for the space between the fingers. FIG. 4b shows an embodiment of the strap element (10b) with a first elastic section (14b), a first inelastic section (15b) formed as a parallelogram, a short intermediate elastic section (16b), a second inelastic section (17b) with a taper and an elastic end section (20b).

Figure 5:
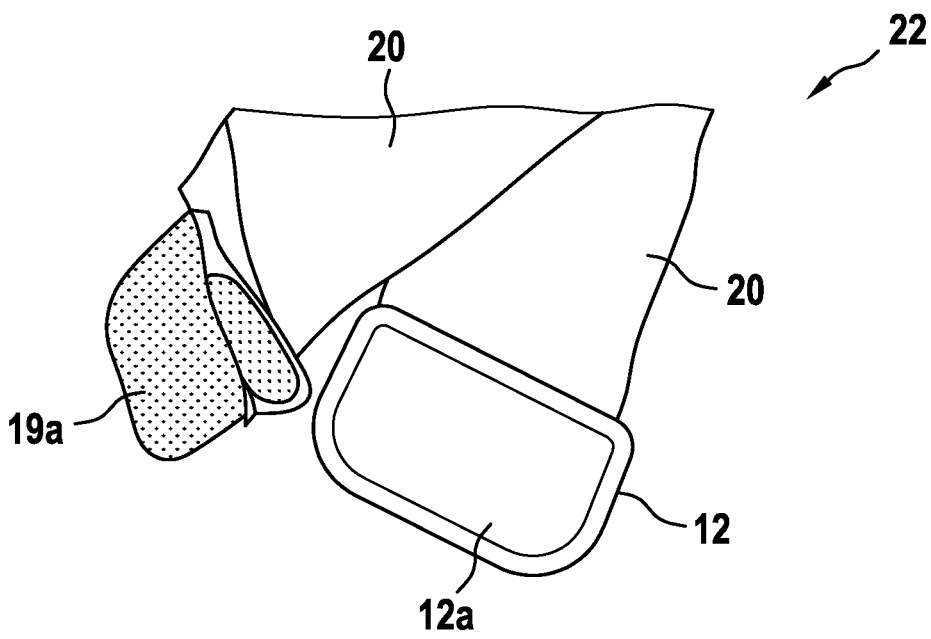
FIG. 5 shows the second part section of the strap element of FIG. 3

FIG. 5 shows the second part section (22) of the strap element with the fourth elastic section (20) at one end of which there is a Velcro® (i.e., hook-and-loop fastener) element (19a) with fish-mouth Velcro® (i.e., hook-and-loop fastener) for securely connecting the second part section (22) to the first part section and at the other end of which there is the second end (12) of the strap element with a Velcro® (i.e., hook-and-loop fastener) element (12a) for fastening to the strap element or to the tube element.

FIGS. 6-10 show various steps in applying the strap element (10) to the tube element (50) of the joint bandage (10) according to the invention.

Figure 6:
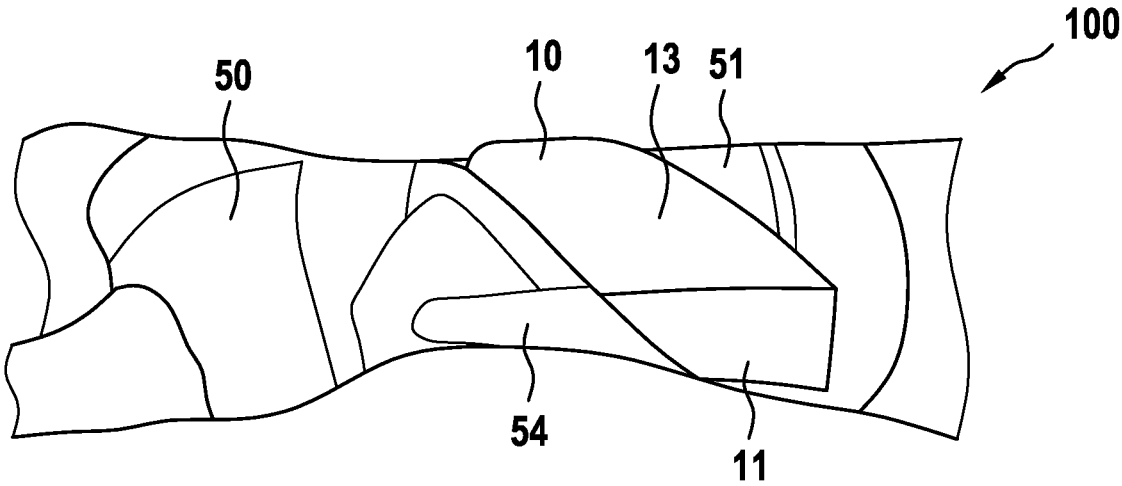
FIGS. 6-10 show different steps in fastening the strap element to the tube element

In FIG. 6, a first step is shown in which the strap element (10) is fastened to the first half (51) of the tube element (50) via a Velcro® (i.e., hook-and-loop fastener) element of the first end (11) of the strap element (10). The first inelastic section (13) runs obliquely distally in the direction of the wrist. A tensioning element (54) inserted into the knitted fabric or applied to the knitted fabric can also be seen, which prevents the stretched tube from being pulled together, but does not contribute to stabilising the joint.

The first end (11) of the strap element (10) is fastened as far away as possible from the pivot point of the wrist. This fixation point can thus create a large lever that restricts the flexion movement very well. The pretension of the strap system can already be adjusted at this point by a more or less strong dorsal extension. The further the user is in dorsal extension at this stage, the more the hand is stabilised. The tighter the basic element (10) is tensioned, the more effectively the bending/falling of the hand is counteracted.

Figure 7:
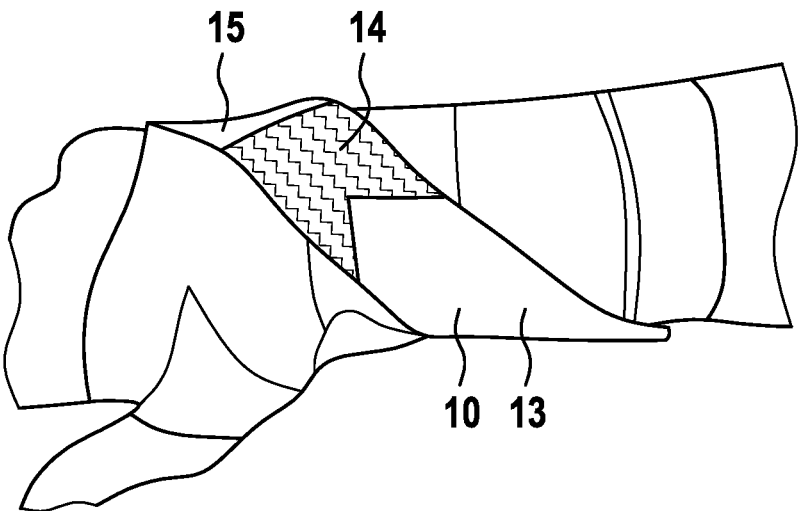

FIG. 7 shows how the strap element (10) is further guided over the back of the hand with the first inelastic section (13)

and the first elastic section (14) on the back of the hand and the second inelastic section (15) on the outer edge of the hand. The strap element (10) is deflected into the palm of the hand as close as possible to the metacarpophalangeal joint of the little finger. This leads to a better force transmission to the wrist. This maximises the leverage effect. At the same time, the position of the strap element (10) at the base joint of the finger is not perceived as disturbing, as the second inelastic section (15) is not perceived as incisive. The first elastic section (14) on the back of the hand also restricts movement in a radial direction to a small extent.

Figure 8:
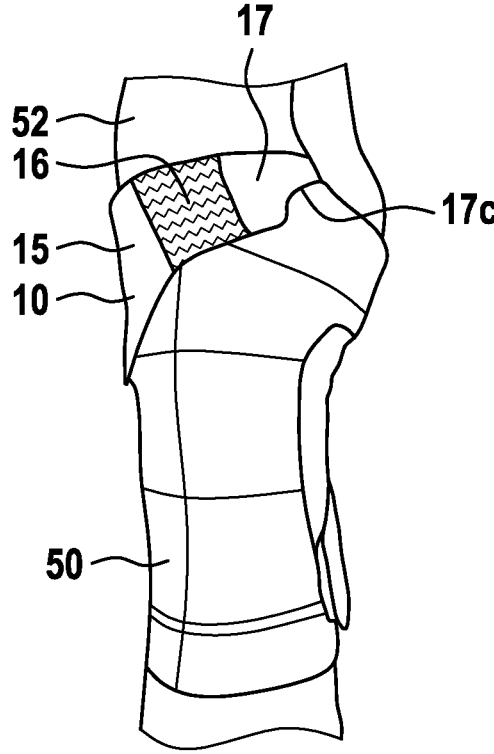

FIG. 8 shows the inside of the hand, where the base element (10) comes from the left side with the second inelastic section (15) and passes through the palm and the second half (52) of the tube element (50) with the second elastic section (16). This is followed by the third inelastic section (17), which is wound with its curved taper (17c) between the thumb and index finger in the direction of the back of the hand. Despite the taper (17c), this section is wide enough and does not cut in, as it is non-elastic. Tensile loads occurring during flexion and spreading are distributed over the largest possible area. Alternatively, the third inelastic section (17) could also be designed as a thumb opening. In this case, the occurring forces would be distributed over the thumb muscles. The third inelastic section (17) also provides a desirable protective posture for the thumb.

Figure 9:
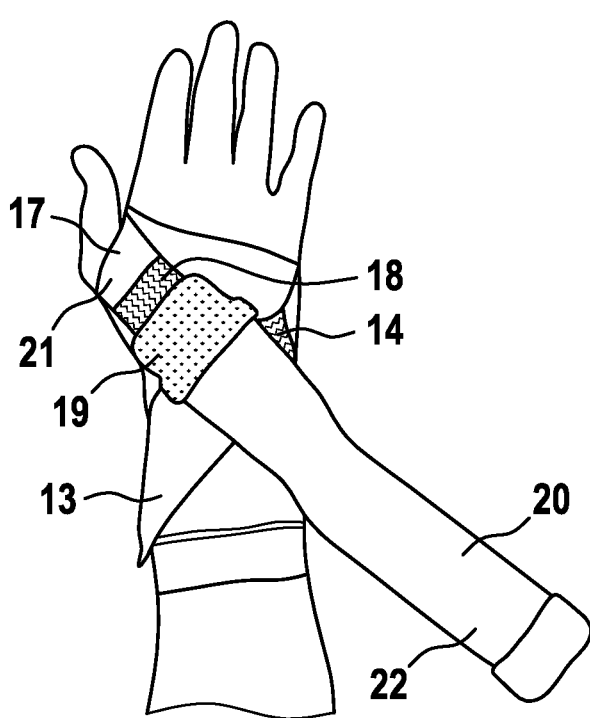

FIG. 9 shows the outside of the hand. The third inelastic section (17) is followed by the third elastic section (18). This allows radial and limited ulnar movement and also contributes to load uptake during flexion. The first part element (21) thus forms a triangle in the hand area that absorbs the flexion movement. The first part element (21) thus ends at the back of the hand and is connected to the second part element (22), which comprises the fourth elastic section (20), via a Velcro® (i.e., hook-and-loop fastener) connection (19).

It can be seen how the third elastic section (18), the Velcro® (i.e., hook-and-loop fastener) element (19) and the fourth elastic section (20) cross the first inelastic section (13) and the first elastic section (14).

Figure 10:
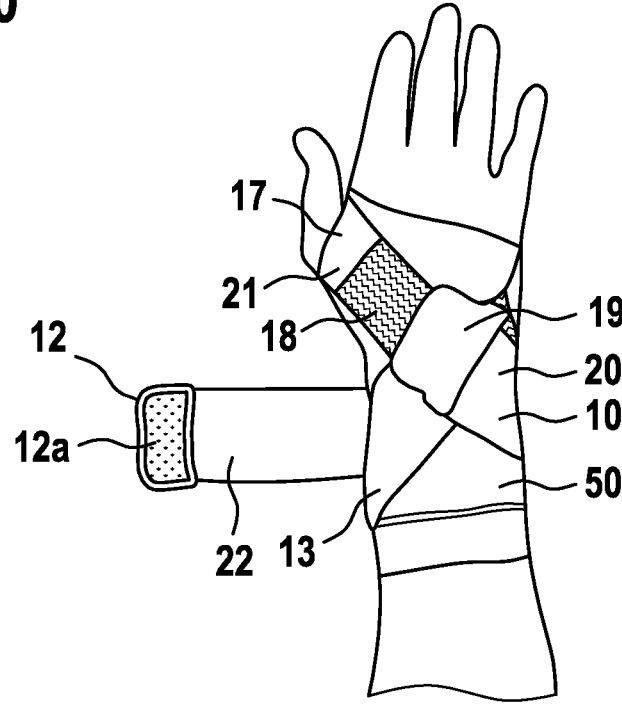

FIG. 10 shows how the fourth elastic section (20) is wrapped around the ulnar edge of the forearm. This radial applying of the second part element (22) can cause additional compression and stabilisation. This also has a stabilising and relieving effect on the carpal tunnel and the carpal ligament. The second part element (22) is fastenable at the second end (12) with the Velcro® (i.e., hook-and-loop fastener) element (12a) there to the strap element (10) or to the tube element (50), so that a strap element course is obtained as shown in FIG. 1.

The division into elastic sections and inelastic sections restricts the force transmission during palmar flexion movement, wherein there is no restriction of the hand movement in dorsal extension. The hand can therefore be moved in this direction without restriction.

Figure 11A:
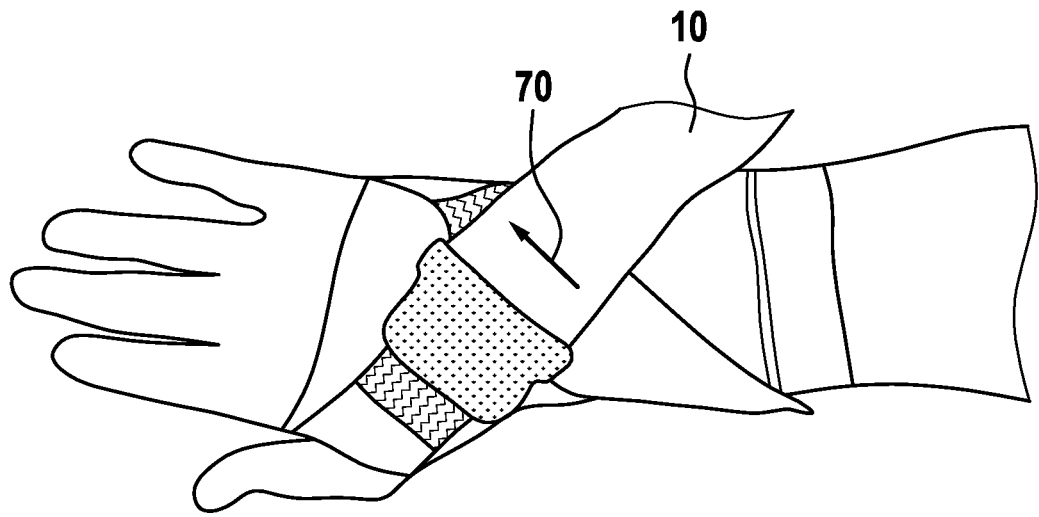
FIGS. 11a-11b show the force transmission when moving the hand
Figure 11B:
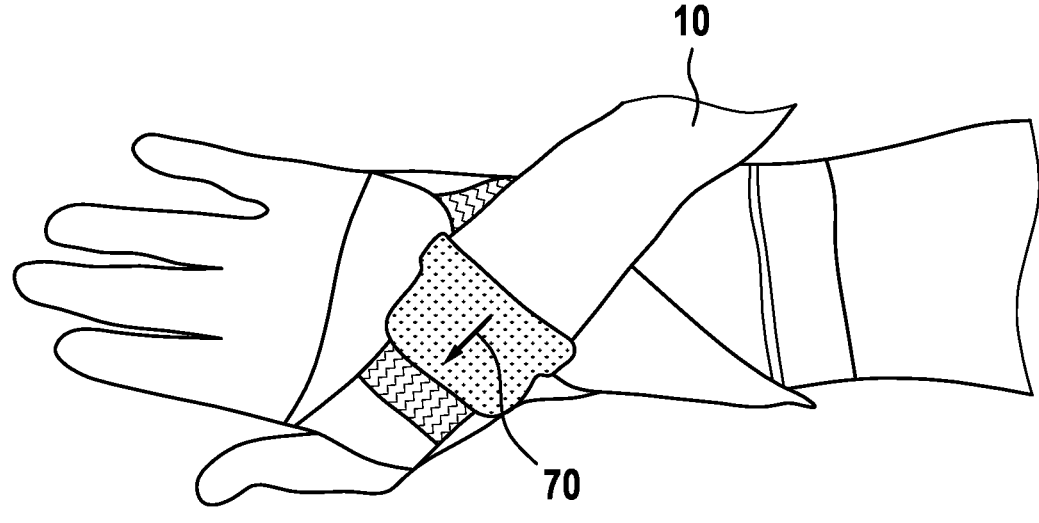
Figure 12:
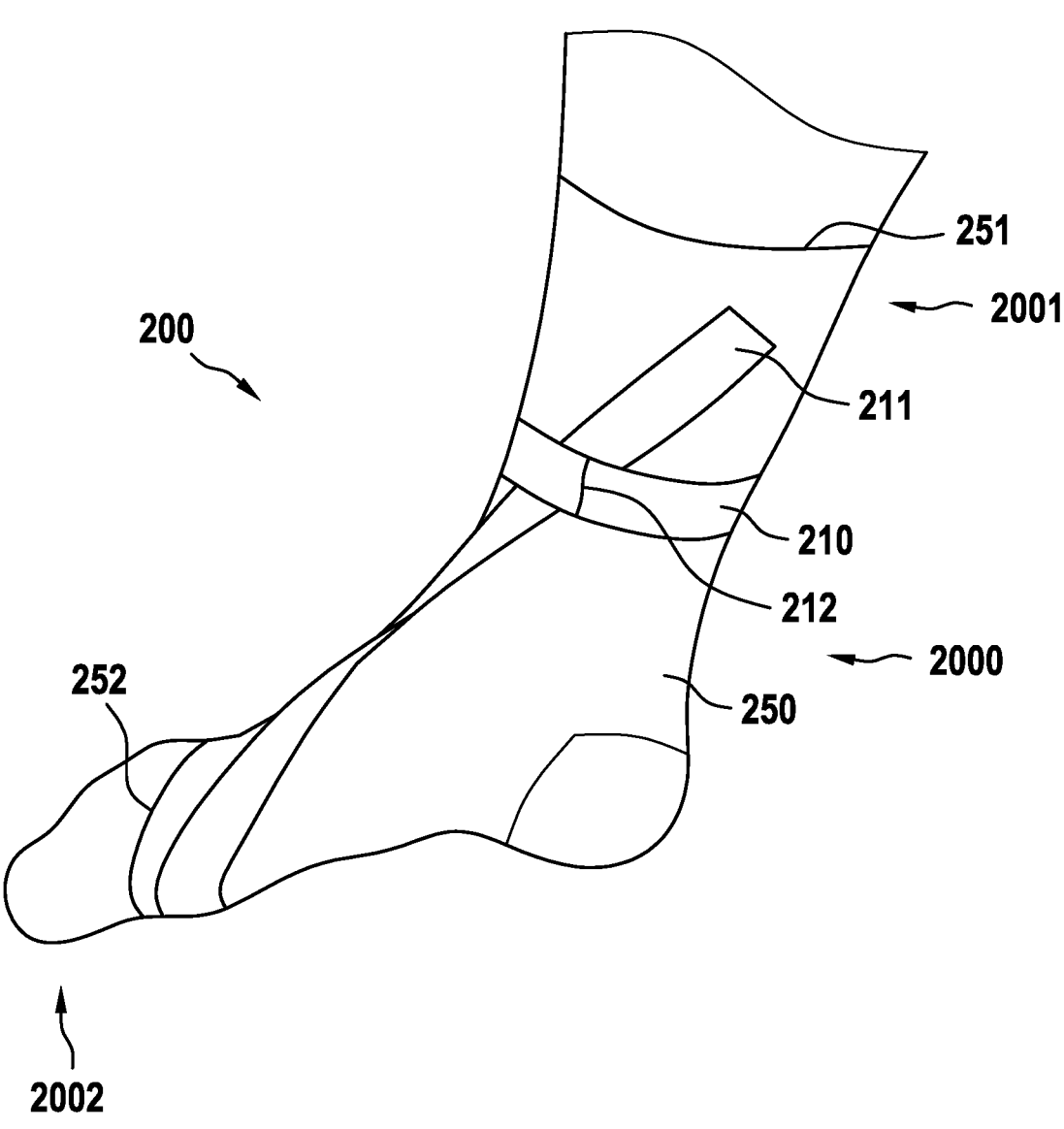
FIGS. 12-16 show schematically different views of an ankle bandage according to the invention
Figure 13:
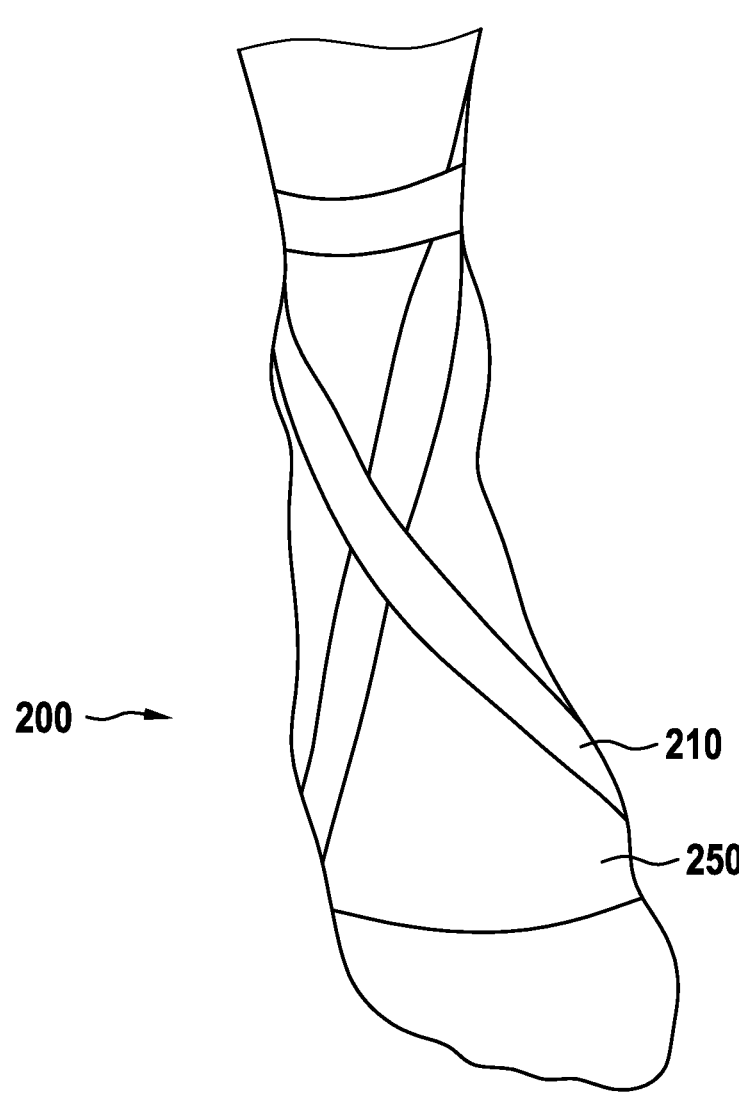
Figure 14:
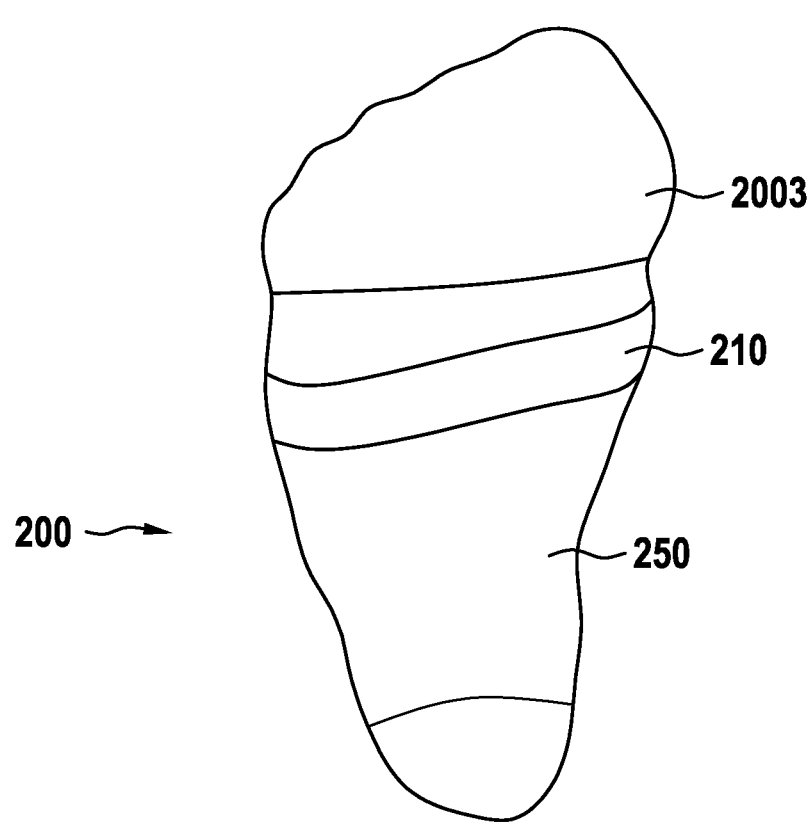
Figure 15:
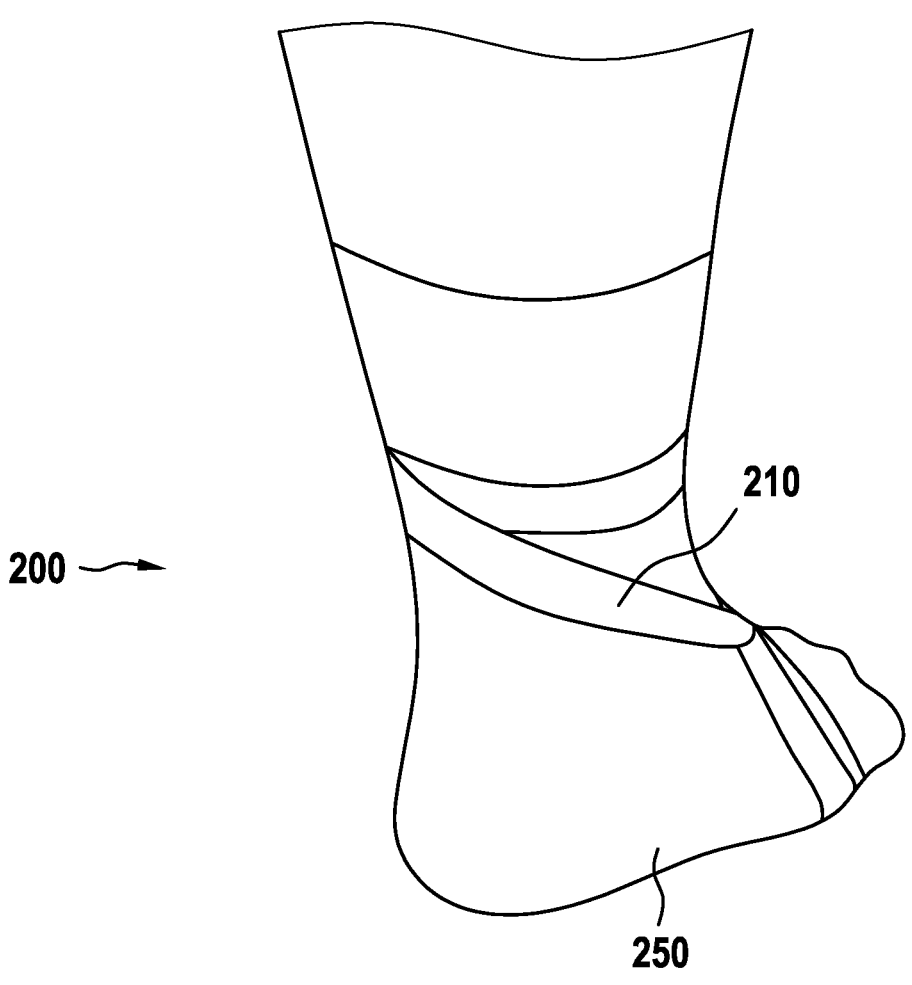
Figure 16:
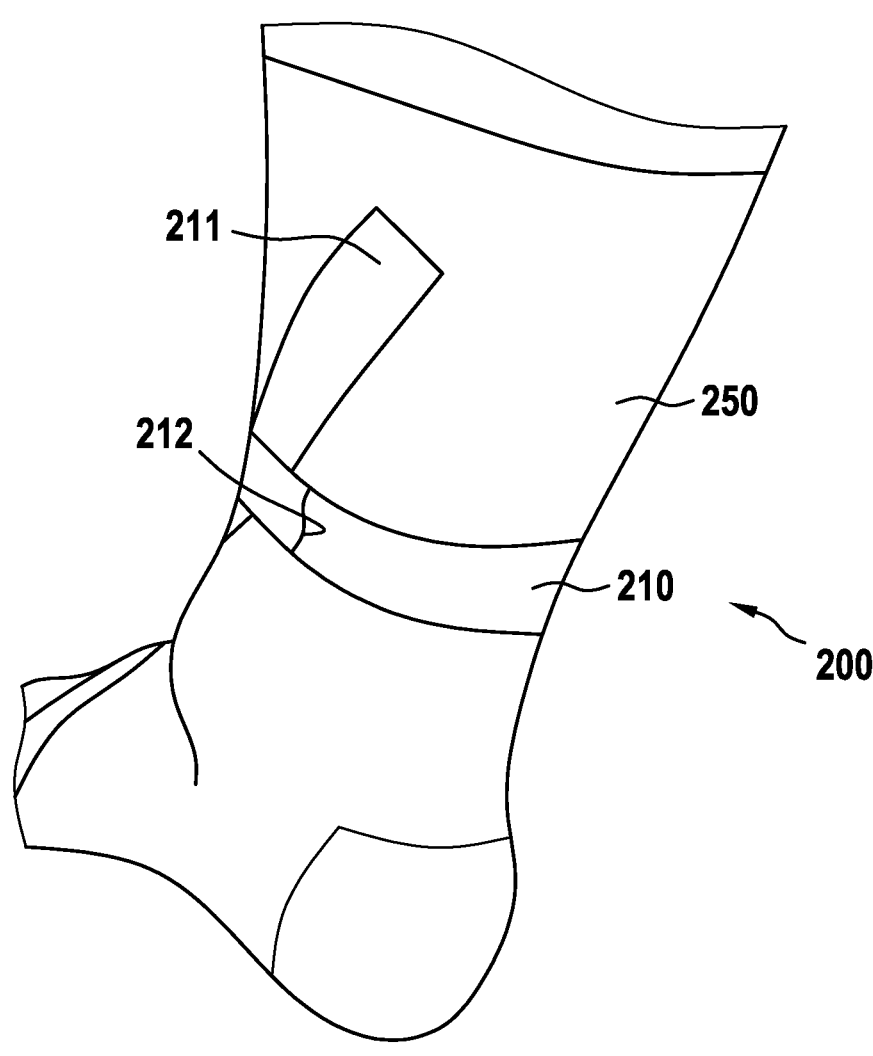

FIG. 11 shows the force transmission (70) of the strap element (10) during a radial (FIG. 11a) or ulnar (FIG. 11b) hand movement. In the case of a radial movement, the force is cushioned by the first elastic section. This allows the movement in a radial direction and merely restricts it in a stabilising manner. When the hand moves in an ulnar direction, the force is cushioned by the third elastic section and the fourth elastic section. These allow the movement in the ulnar direction and only restrict it in a stabilising manner.

FIGS. 12 to 16 schematically show an ankle bandage (200) according to the invention in the embodiment with tube element (250) on a right ankle (2000). A strap element (210) according to the invention is fastened to the tube element (250), which is placed around the area of the lower leg (2001) adjacent to the ankle (2000), the ankle (2000) and the foot (2002) to stabilise the ankle (2000). The tube element (250) has a first tube half with a first end (251) and a second tube half with a second end (252), wherein the strap element (210) has a first end (211) and a second end (212), wherein the first end (211) of the strap element (210) is fastened to the first tube half (251) via a Velcro® (i.e., hook-and-loop fastener) connection, wherein the second end (212) of the strap element (210) is reversibly fastenable to the strap element (210) or to the first tube half (251) via a Velcro® (i.e., hook-and-loop fastener) connection and is presently fastened to the strap element (210). The first end of the strap element (210) is fastened to the first tube half (51) and positioned on the lower leg (2001). The strap element (210) runs from the first end distally across the ankle (2000) to the back of the foot (2002), runs around the foot (2002) on the sole of the foot (2003). From there, the strap element (210) runs dorsally back over the ankle (2000) to the lower leg (2001), thereby crossing itself. The strap element (210) then wraps around the lower leg (2001) and is Velcro® (i.e., hook-and-loop fastener) ed to itself with the second end (212) in the area of the lower leg near the ankle.

The course of the strap element (210) shown here thus corresponds to the course of the strap element on the hand shown in FIGS. 1 to 11, except that the strap element does not run in the space between the big toe and the adjacent toe, wherein such a configuration is also possible. The strap element (210) again has elastic and non-elastic sections, the positioning of which in relation to the foot and the leg corresponds to the positioning of the sections shown above in relation to the hand and the arm. For example, the section on the sole of the foot is elastic, as is the second end region of the strap element, but the sections on the sides of the foot are inelastic. In the present embodiment, the strap element (210) is in a single piece and has no separable sub-elements. The skilled person can transfer all other aspects of the exemplary wrist bandage (100) shown to the ankle bandage (200).

Figure 17A:
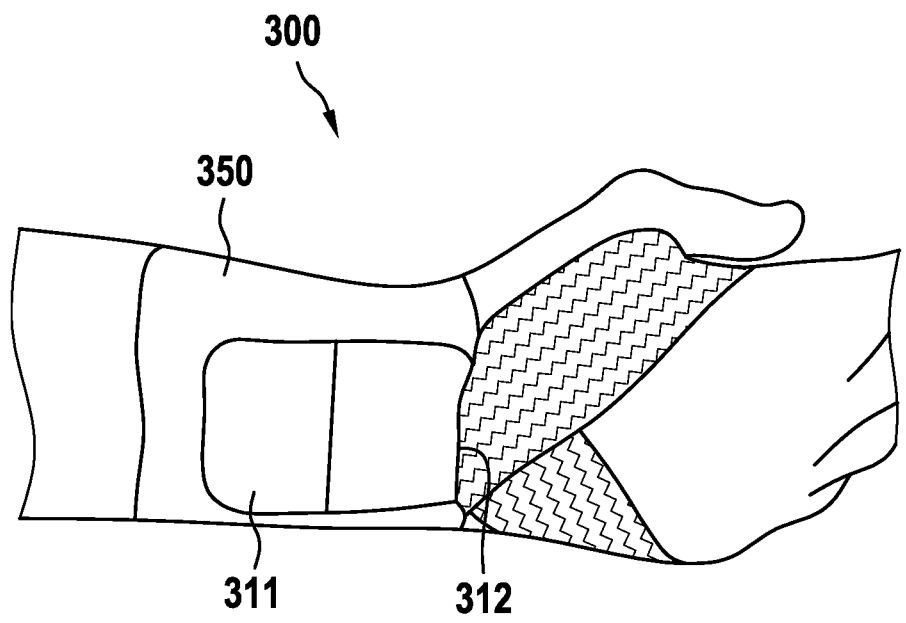
FIGS. 17a-17b show an alternative embodiment of the wrist bandage
Figure 17B:
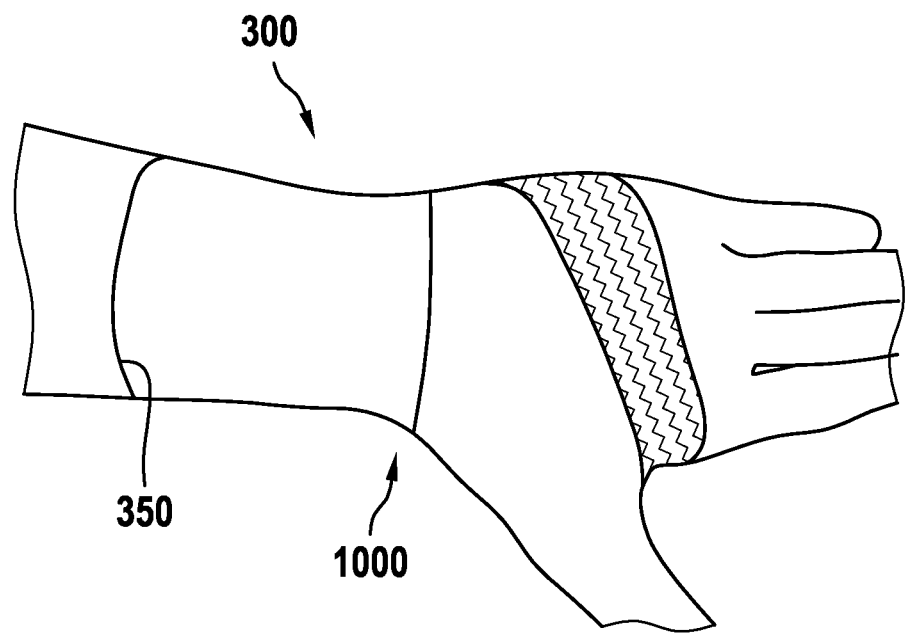
Figure 18A:
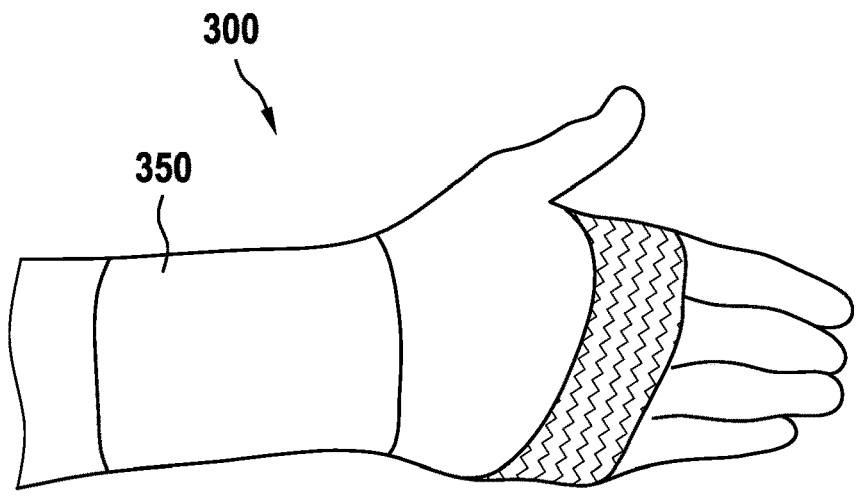
FIGS. 18a-18b shows a further possible use of the alternative embodiment from FIG. 17
Figure 18B:
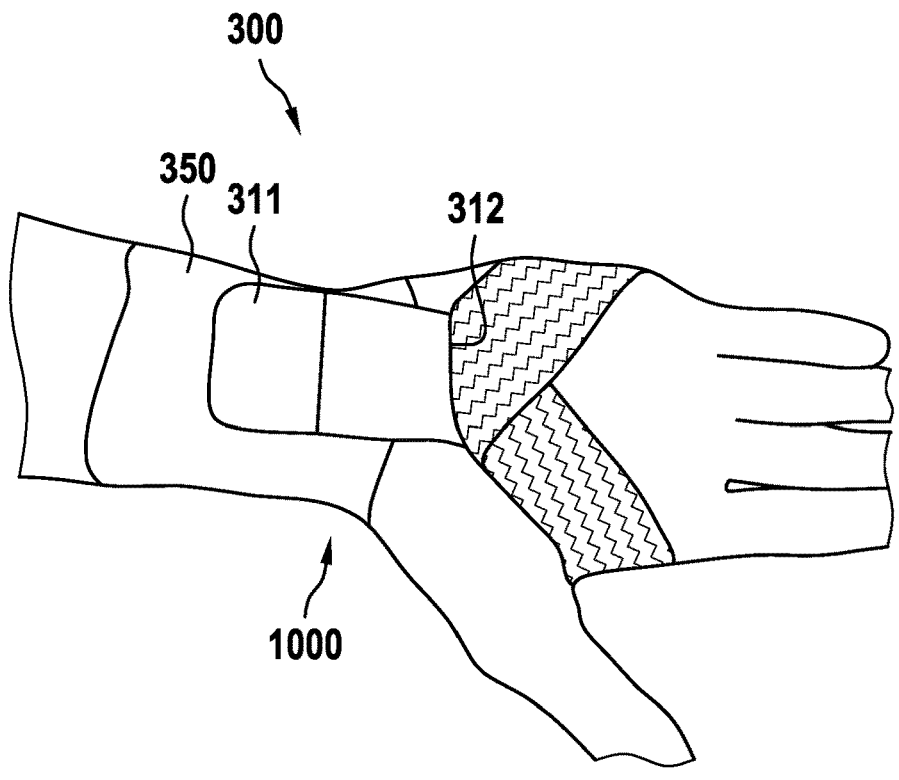

FIGS. 17 and 18 schematically show a further embodiment of the wrist bandage (300) according to the invention in the embodiment with a short tube element (350) on a right wrist (1000). A strap element (310) according to the invention is fastened to the tube element (350). FIGS. 17a and 18a show the wrist bandage (300) on the back of the hand and FIGS. 17b and 18b show the wrist bandage (300) on the palm of the hand. The strap element (310) has a first end (311) and a second end (312), wherein the first end (311) of the strap element (310) is fastened to the tube element (350) via a Velcro® (i.e., hook-and-loop fastener) connection, wherein the second end (312) of the strap element (310) is fastened to the strap element (310). No stabilising bar is required for this bandage either.

The strap element 310) again has elastic and non-elastic sections which, in terms of their positioning in relation to the hand and arm, correspond in principle to those of the wrist bandage of FIGS. 1 to 11, even if the course of the strap element is different. For example, the section on the palm of the hand in FIG. 17b and on the back of the hand in FIG. 18a is elastic, as is the second end region of the strap element, but the sections on the sides of the hand are inelastic. In the present embodiment, the strap element (210) is in single piece and has no separable sub-elements. The skilled person can transfer all other aspects of the exemplary wrist bandage (100) to the embodiment (300) shown here.

The invention claimed is:

1. A joint bandage configured to be for a wrist or an ankle, comprising a strap element with a first end and a second end, wherein the second end of the strap element is fastened or reversibly fastenable to the strap element or to a tube element, characterized in that, the strap element successively has a first elastic section, a first non-elastic section, a second elastic section, a second non-elastic section and a third elastic section, wherein the first non-elastic section has a section in the form of shape which comprises one of a parallelogram, a curvature, or a kink configured to position the first end of the strap element offset from and parallel to the second end of the strap element, and wherein the second non-elastic section has a taper.

2. The joint bandage according to claim 1, wherein the first end of the strap element is configured to run around a zygopodium, such that the first end of the strap element is fixable to the zygopodium.

3. The joint bandage according to claim 2, wherein the first end of the strap element is configured to be fastenable to the zygopodium, wherein, in an applied state of the strap element, the strap element is configured such that: the first end of the strap element is positioned on the zygopodium and the strap element runs from the first end of the strap element distally over an extremity end joint to a basipodium, around the basipodium on an inside of the basipodium, dorsally over the basipodium to the zygopodium, thereby forming an overlapping portion of the strap element, and runs around the zygopodium, wherein the first end of the strap element is reversibly fastened to the strap element with the second end in an area of the zygopodium.

4. The joint bandage according to claim 1, wherein the strap element comprises (i) a first part including the first end, the first elastic section, the first non-elastic section, the second elastic section, the second non-elastic section, and the third elastic section, and (ii) a second part including a fourth elastic section, the second part is connectable to the first part at the third elastic section.

5. The joint bandage according to claim 4, wherein the first part and the second part are reversibly interconnectable at the third elastic section via a hook and loop fastening mechanism of the fourth elastic section, and wherein the hook and loop fastening mechanism of the fourth elastic section on the second part is reversibly fastenable to the tube element without the first strap part element.

6. The joint bandage according to claim 1, wherein the second end of the strap element is reversibly fastenable to the strap element.

7. The joint bandage according to claim 1, wherein the elastic tube element has a first tube half with a first end and a second tube half with a second end, wherein the first end of the strap element is fastenable to the first tube half, wherein the second end of the strap element is reversibly fastenable to the strap element or to the first tube half, characterised in that, in an applied state of the strap element, the strap element is configured such that: the first end of the strap element is fastened to the first tube half and is positioned on a zygopodium and the strap element runs from the first end of the strap element distally over an extremity end joint to a basipodium, around the basipodium on an inside of the basipodium, dorsally over the extremity end joint to the zygopodium, thereby forming an overlapping portion of the strap element, and runs around the zygopodium, wherein the first end of the strap element is reversibly fastened to the strap element or to the first tube half with the second end in an area of the zygopodium.

8. The joint bandage according to claim 1, wherein at least one elastic section of the strap element is configured to run over a back of a hand, or a palm of the hand, or over a back of a foot, or a sole of the foot, and/or wherein at least one non-elastic section of the strap element is configured to run along one or more edges of the hand or one or more edges of the foot.

9. The joint bandage according to claim 1, wherein the taper of the second non-elastic section comprises an arch.

10. The joint bandage according to claim 1, wherein the section of the first non-elastic section is comprises a kink.

11. The joint bandage according to claim 1, further comprising a fourth elastic section associated with the third elastic section.

12. The joint bandage according to claim 1, wherein a third non-elastic section is further associated to the first elastic section.

13. The joint bandage according to claim 1, wherein the second end of the strap element further comprises a connecting element, such that the second end of the strap element is fastenable to the tube element without the first end of the strap element.

14. The joint bandage according to claim 1, wherein the joint bandage does not have a stabilising bar.

* * * * *